(12) United States Patent
Zemer et al.

(10) Patent No.: US 6,654,115 B2
(45) Date of Patent: Nov. 25, 2003

(54) SYSTEM AND METHOD FOR MULTI-DIMENSIONAL OPTICAL INSPECTION

(75) Inventors: Dan Zemer, Rehovot (IL); Michael Faibisch, Givat Zeev (IL)

(73) Assignee: Orbotech Ltd., Yavne (IL)

(*) Notice: Subject to any disclaimer, the term of this patent is extended or adjusted under 35 U.S.C. 154(b) by 0 days.

(21) Appl. No.: 10/032,060

(22) Filed: Dec. 31, 2001

(65) Prior Publication Data

US 2002/0093650 A1 Jul. 18, 2002

Related U.S. Application Data

(60) Provisional application No. 60/262,103, filed on Jan. 18, 2001.

(51) Int. Cl.[7] .............................................. G01N 21/00
(52) U.S. Cl. ................................................... 356/237.5
(58) Field of Search ........................... 356/237.1–237.5

(56) References Cited

U.S. PATENT DOCUMENTS

| | | | |
|---|---|---|---|
| 4,650,333 A | 3/1987 | Crabb et al. ................ 356/376 |
| 4,657,396 A | 4/1987 | Honda et al. ............... 356/394 |
| 4,674,869 A | 6/1987 | Pryor et al. .................... 356/1 |
| 4,677,302 A | 6/1987 | Chiu et al. ................... 250/560 |
| 4,900,146 A | 2/1990 | Penney et al. ................. 356/1 |
| 5,011,960 A | 4/1991 | Ando et al. ................. 356/376 |
| 5,088,828 A | 2/1992 | Doemens et al. ........... 356/376 |
| 5,200,799 A | * | 4/1993 | Maruyama et al. ......... 356/394 |
| 5,455,870 A | * | 10/1995 | Sepai et al. ................. 382/147 |
| 5,489,985 A | * | 2/1996 | Mochida et al. ............ 356/398 |
| 5,812,269 A | * | 9/1998 | Svetkoff et al. ............ 356/602 |
| 6,028,673 A | * | 2/2000 | Nagasaki et al. ........... 356/608 |
| 6,084,663 A | * | 7/2000 | Seng ........................ 356/237.4 |
| 6,522,777 B1 | * | 2/2003 | Paulsen et al. ............. 382/154 |

FOREIGN PATENT DOCUMENTS

WO      WO 01/43521      6/2001

* cited by examiner

*Primary Examiner*—Michael P. Stafira
(74) *Attorney, Agent, or Firm*—Sughrue Mion, PLLC

(57) ABSTRACT

An optical inspection system has a topology sensing assembly. A height detector detects whether a region of a circuit has a height different from a height of the surface, and provides height data. A topology representation of the circuit, based on the height data, forms the basis for a reduced representation of the topology, and subsequent defect analysis.

38 Claims, 3 Drawing Sheets

SYSTEM AND METHOD FOR MULTI-DIMENSIONAL OPTICAL INSPECTION

CROSS-REFERENCE TO RELATED APPLICATIONS

This application claims the benefit of U.S. Provisional Application No. 60/262,103, filed Jan. 18, 2001, which is incorporated by reference, herein, in its entirety.

FIELD OF THE INVENTION

The present invention relates generally to automated optical inspection (AOI) systems and particularly to an AOI system for inspecting electrical circuits such as printed circuit boards (PCBs) of any kind, including interconnect packaging substrates (ICP), flat panel displays (FPDs) and integrated circuits.

BACKGROUND OF THE INVENTION

Automated optical inspection (AOI) systems are used to inspect various kinds of articles and electrical circuits, including the surfaces of FPDs, the surfaces of individual laminate layers of PCBs and ICPs prior to lamination (sometimes called inner layers), the surfaces of already laminated multi-layer PCBs and ICPs (sometimes called outer layers), the surfaces of electrical circuits having solder paste deposits formed thereon, and electrical circuits having electronic components mounted thereon. In general, electrical circuits such as PCBs, ICPS, FPDs and integrated circuits, are formed by selectively depositing a reflective conductor on a substrate.

In conventional AOI systems portions of the surface of an electrical circuit under inspection are successively illuminated with a thin line of intense light. Alternatively, the surface may be illuminated by a scanning laser beam. The intensity of reflected light, or of fluorescent light, in response to the illumination, is detected and registered for elemental spatial portions over the X-Y plane of the surface of the circuit to form an image of the electrical circuit surface. The image is suitably processed and analyzed with reference to a non-defective image, for example an image derived from a Computer Aided Drawing or Manufacturing (CAD or CAM) data base in order to locate the presence of defects in the electrical circuit.

BRIEF SUMMARY OF THE INVENTION

One general aspect of the present invention relates to a system and methods for inspecting an electrical circuit for defects employing a three-dimensional topographical representation of an electrical circuit under inspection. The topology representation is processed and analyzed to detect the presence of defects in the planar geometric shape of the electrical circuit. Optionally, the height information is also processed to determine the presence of defects at selected locations along the surface of the electrical circuit.

In accordance with an embodiment of the invention, height data in the topology representation is transformed into a reduced information mapping of the electrical circuit indicating the planar locations, that is location in an X,Y plane, of electrical circuit features having a predetermined height attribute. In other words, a volume representation of height is transformed into a representation of planar location. For example, the reduced information mapping may appear as a planar map of the locations of any portions of the electrical circuit that are either raised or depressed with respect to the surface of a substrate. Optionally, the reduced information mapping differentiates between those portions that are raised with respect to the surface of the substrate and those portions that are depressed with respect to the surface.

Such a reduced information mapping is analyzed by a defect analyzer with reference to a corresponding representation of a known non-defective electrical circuit determine the presence of defects in the electrical circuit. The representation of a non-defective circuit may be obtained either by acquiring a representation of a known to be non-defective electrical circuit, or by derivation from a CAD or CAM computer file. Typically analysis includes confirming that all elements forming the electrical circuit are present, that the elements are properly formed and that no extraneous elements are present in the circuit.

In accordance with another embodiment of the present invention, the topology representation, or selected parts thereof, is provided to a height processor operative to analyze the topology representation, or selected parts thereof, for height defects. Height defects may include, for example, conductors and parts of conductors (hereinafter referred to together as "conductors" for the sake of generality) having a height that is different from a specified height, or holes whose depth is different than a specified depth. Optionally, analysis of height defects may include distinguishing between real height defects, such as an undesired formation of a copper conductor, and non-height defects such as dust. In accordance with an embodiment of the invention, the height processor analyzes only selected portions of the electrical circuit which have been indicated as necessitating height processing. Such indication may be provided by the defect analyzer, for example based on defects in the planar formation of an electrical circuit, or by an input from a CAM reference indicating a region of the electrical circuit requiring inspection for possible height defects.

In accordance with an embodiment of the invention, height detection can be carried out using illumination provided by any suitable coherent or non-coherent, monochromatic or polychromatic light source, or any other suitable source of electromagnetic radiation.

BRIEF DESCRIPTION OF THE DRAWINGS

The present invention, and its further aspects and advantages, will be understood and appreciated more fully from the below detailed description, taken in conjunction with the enclosed drawings, in which.

DETAILED DESCRIPTION

The invention will now be described more fully by way of various exemplary embodiments. It is understood that the embodiments are described for the sake of explanation only, and do not limit the true scope of the invention, which scope is defined in the claims appended below. In these examples, many specificities are included for the sake of completeness, and others are omitted so as to avoid obscuring the key teaching points.

Figures 1A, 1B:
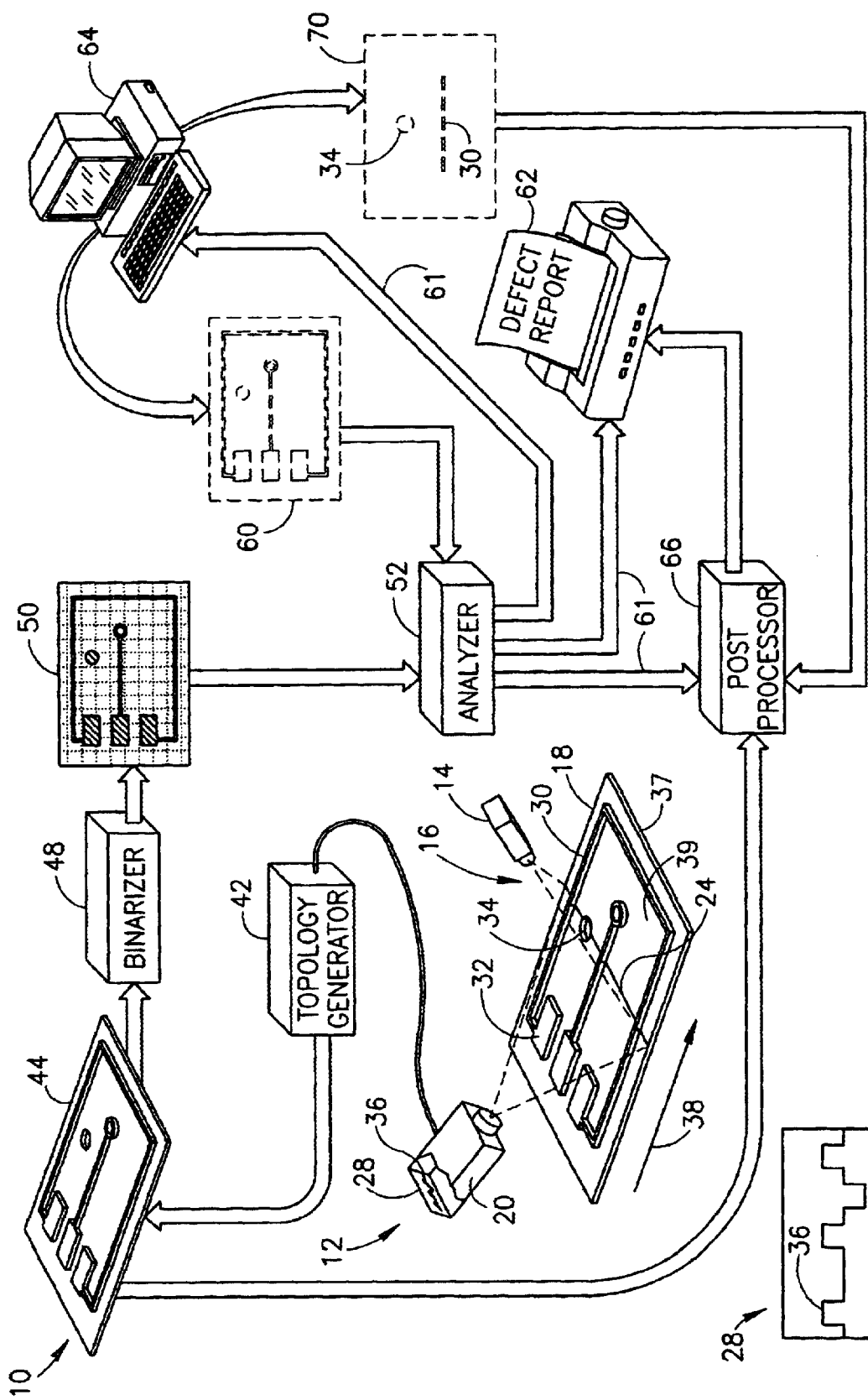
FIG. 1A is a simplified pictorial illustration of an automated optical inspection system constructed and operative in accordance with an embodiment of the present invention.
FIG. 1B is an enlarged schematic illustration of the height signal seen in the sensor shown in FIG. 1A.
Figure 2:
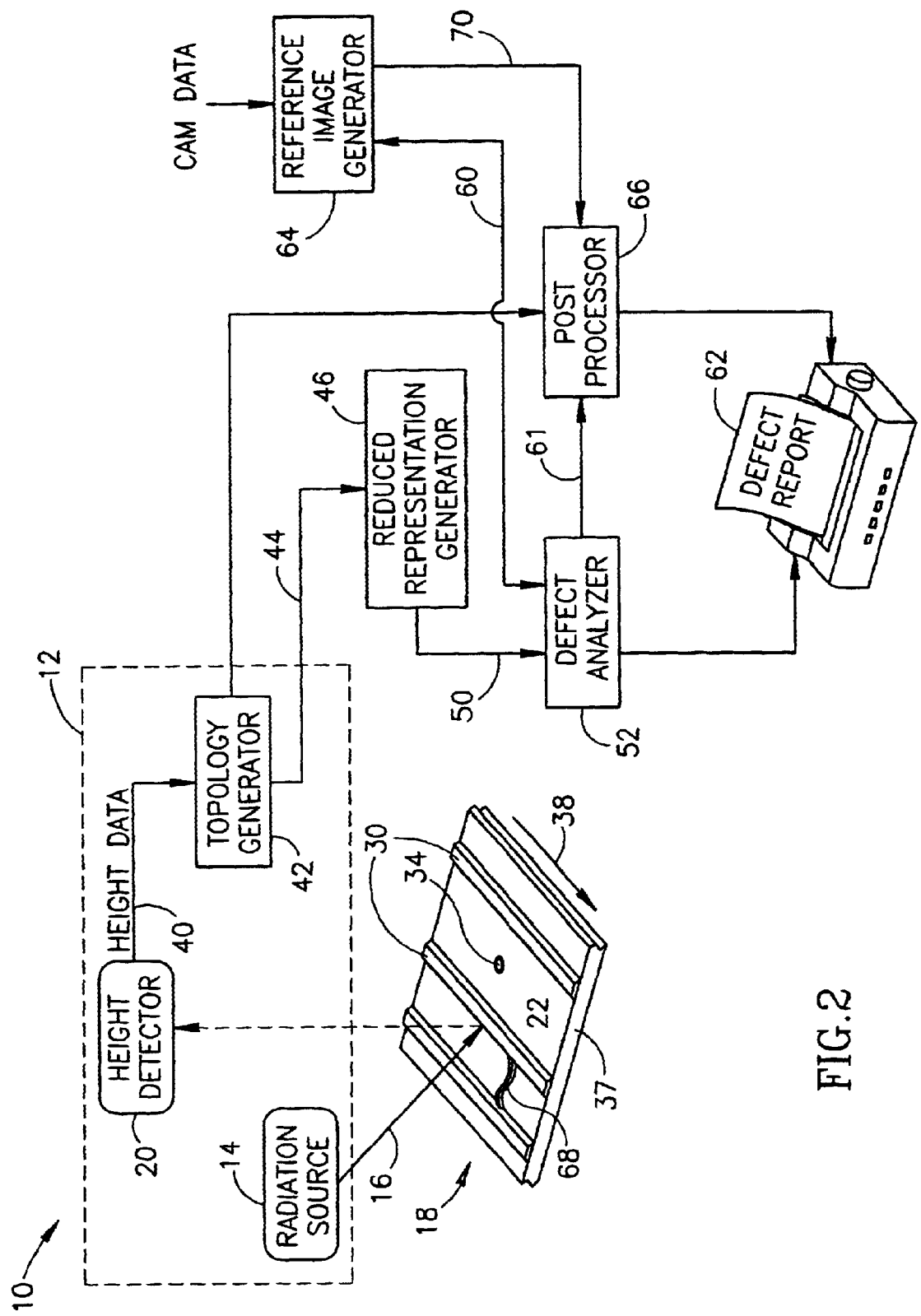
FIG. 2 is a simplified block diagram illustration of the automated optical inspection system of FIG. 1.

Reference is now made to FIGS. 1A, 1B and 2 which illustrate an example of an automated optical inspection system 10 constructed and operative in accordance with an embodiment of the present invention.

The system 10 may include a topology sensing assembly 12 including a source 14 of electromagnetic radiation for delivering a radiation beam 16 onto an article to be inspected 18, such as an electrical circuit, and at least one height detector 20 for detecting (or making a determination as to) the height of elemental regions of a surface 22 of electrical circuit 18 in a non-contact manner.

For the purpose of this example, the exemplary radiation source 12 may be understood to be a laser such as a doubled or tripled YAG laser or Cd:He laser. The invention is not limited to this source, but encompasses any kind of suitable radiation source providing any type of radiation.

Indeed, various parts of the invention can be carried out with various coherent or non-coherent, monochromatic or polychromatic illumination, or any other suitable electromagnetic radiation, in conjunction with a suitable height detector. Moreover, the invention may be carried out with any suitable non-contact or contact based probe.

As seen in the example of the embodiment of FIG. 1A, radiation beam 16 is shaped into a substantially uniform line of light 24, for example by a suitable structured light projector (not shown). One concrete example of such a structured light projector (among many) is a model 501L structured light projector available from LASIRIS of Canada.

As seen in the example of the embodiment of FIG. 1A, line 24 is viewed by a suitable height detector 20. One concrete example of a suitable height detector (among many possible) is a MAPP range profiling camera available from IVP of Sweden. Alternatively, any suitable sensors, such as the MV40 sensor available from Photobit of California, in conjunction with suitable optics and a suitable height profiling image processor, may be employed.

It is appreciated by persons familiar with this field that, where either beam 16 is projected at a non-normal angle to surface 22 and/or where height detector 20 views surface 22 at a non-normal angle, then where surface 22 is flat, the line of light 24 is imaged onto a sensor portion 28 of detector 20 as a straight line. Where surface 22 has a surface relief (for example because of conductors 30, integrated circuits 32, or vias 34 located along surface 22), however, a non straight line exhibiting various protrusions 36 is imaged onto sensor portion 28. An enlarged view of line 24, imaged onto sensor 28 as a non-straight line exhibiting protrusions 36, is seen in FIG. 1B. Protrusions 36 are converted into height data for elemental regions of surface 22 by any suitable calculation as known in the art, such that each elemental region along surface 22 is provided with a coordinate and a height dimension.

It is noted that the surface 22 of an electrical circuit 18 typically includes some portions that are reflective such as at conductors 30, and some portions that are diffusive such as at substrate 37. Typically, reflection of light from line 24 provides a suitable indication of the height dimension of reflective portions, such as conductors 30. At non-reflective portions, such as substrate 37, typically no indication of height dimension is provided due to insufficient reflected light intensity, scattering or other optical affects. It is appreciated that this result normally is beneficial in electrical circuit inspection inasmuch as height variations in substrate 37 typically are of insignificant interest.

In accordance with an embodiment of the invention, a displacement subsystem (not shown) is provided to introduce relative displacement between topology sensing assembly 12 and electrical circuit 18, in a direction such as indicated by arrow 38, in order to obtain height data for elemental regions covering substantially the entirety of surface 22. It is appreciated that elemental regions are virtual regions (like pixels) that in reality do not exist on surface 22, but rather correspond to elements in an image or map of surface 22 to which one or more properties, such as a representative height, can be assigned.

Height data 40 for a plurality of elemental regions disposed along surface 22 is supplied to a topology generator 42 which collects the height data 40 to provide a topology representation 44 of surface 22, which may be supplied to a reduced representation generator 46 (FIG. 2) such as binarizer 48 (FIG. 1A). Additionally, topology representation 44 may be stored in a buffer (not shown) for further analysis.

It is appreciated that the functionality of the topology generator 42 may be an integral part of topology sensing assembly 12 as seen in FIG. 2, or it may be provided in a separate computational unit, e.g., as part of an image analysis computer that is separate from the sensor.

Topology representation 44 may be supplied to reduced representation generator 46 (shown in the example in FIG. 1A as a binarizer 48 which produces a binary map of surface 22). Preferably, topology representation 44 is provided to reduced representation generator on the fly, at substantially the same rate as height data is streamed to topology generator 42. Reduced representation generator 46 is operative to transform the height information contained in topology representation 44 into a reduced data representation 50, such as a planar binary representation, of surface 22.

The reduced data representation 50 may be received by defect analyzer 52, which inspects reduced data representation 50 to detect various defects in electrical circuit 18. Such defects include the proper planar formation and location of elements forming electrical circuit 18.

In an embodiment of the invention, reduced data representation 50 is a digital representation of surface 22, and provides a substantially planar representation of various features, namely various electrical circuit elements, such as conductors 30, integrated circuits 32, and vias 34 along surface 22, without an indication of a height dimension. Reduced data representation 50 may be a binary representation showing the geometric formation and planar location of any element extending above or below the plane of the surface of substrate 37. Alternatively and additionally, reduced data representation 50 may provide an indication of contours (not shown), which are the locations of transitions between substrate 37 and various elements on surface 22 (such as conductors 30, integrated circuits 32, vias 34 or solder past formations).

It is appreciated that, still alternatively, reduced representation 50 may provide a reduced, but non-binary, representation such as a representation that separately indicates the locations of features which extend above surface 22 (such as conductors 30, integrated circuits 32 and solder past formations), and the locations of features which extend below surface 22 (such as vias 34).

Figure 3:
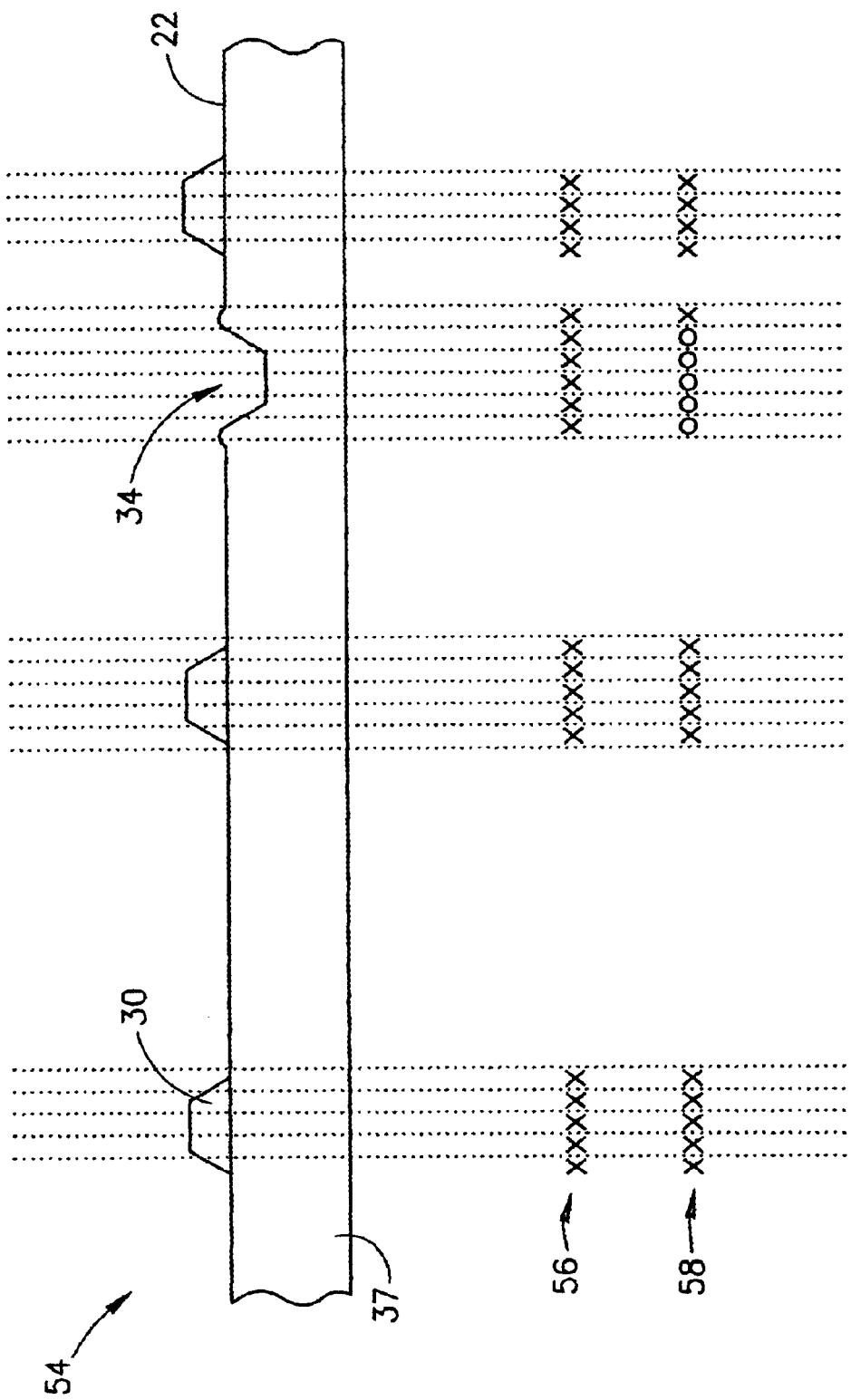
FIG. 3 is a simplified illustration of a section of a topographical map and a corresponding planar map of the same section in accordance with an embodiment of the present invention.

Reference is made to FIG. 3, which is a simplified illustration of a section 54 of electrical circuit 18 illustrating the topology thereof, and a corresponding binary representation 56 and a corresponding reduced but multi-population (non-binary) representation 58 of surface 22 along section 54. Conductors 30 extend above substrate 37, while via 34 includes an annular ring portion that extends above substrate 37 and another portion that extends below surface 22 to form a depression into substrate 37.

In binary representation 56, only the planar location of conductors 30 and via 34 is shown, and no indication of height or depth is provided. In the multi-population representation 58, the planar location of conductors 30 is shown and indicated as being above the surface of substrate 37 by an "X". Additionally, in multi-population representation 58 the planar location of a via 34 is shown and indicated as extending below surface 22 of substrate 37 by a "0". Other forms electrical circuit elements that may extend below the surface of substrate 37 include, for example, blind vias, through holes, and flex connectors. It is appreciated that a multi-population 58 may also include some indication of degree of height than topology representation 44.

By assuming that edges of conductors typically are uniformly sloped, and that the height is sampled at some discrete location along a sloped edge, the planar resolution of reduced representation 50 may be enhanced compared to the planar resolution of topology representation 44 by transforming height data into enhanced spatial information.

For example, techniques used to enhance the spatial resolution of gray scale images may be employed. Such techniques typically involve the analysis of characteristics of neighborhoods of elemental areas. It is appreciated that methodologies employed in the spatial resolution enhancement of optical gray scale images which employ gray scale image data to enhance spatial location information, exemplified by U.S. Pat. No. 5,774,572 to Caspi, the disclosure of which is incorporated by reference for its useful background information on this point, may be adapted to use height information contained in topology representation 44 to enhance the spatial resolution of reduced data representation 50. It is appreciated that other methods of image enhancement, employed in enhancing optical images, such as adaptive threshold methods, may be suitable to enhance the resolution of reduced representation 50 as a function of height information contained therein.

Returning now to FIGS. 1 and 2, defect analyzer 52 receives a reference image 60 corresponding to the electrical circuit 18 being inspected. Defect analyzer 52 is operative to analyze the reduced information image 50 with reference to the reference image 60 to detect at least some types of defects in electrical circuit 18. The types of defects that typically may be detected in analyzer 52 include (but are not limited to):

the presence of all desired features on electrical circuit 18, such as conductors 30, vias 34, or solder paste deposits (not shown), the proper location of such features, the proper spatial formation and geometrical parameters of such features, e.g. pad size and conductor width, and the absence of extraneous features.

Extraneous features may include, for example, shorts or opens. Of particular interest are fine opens (not shown) which are very delicate breaks or cracks in conductors and fine shorts 68 (FIG. 2) which are very small undesired interconnections, between conductors 30. Such fine short defects, for example, result in the recording of a height dimension at the particular location.

Given the reference image 60, the defect analyzer could, e.g., note a difference between the expected reading of no height for a given location, compared to a detected reading of a non-zero height at the location, and generate a defect indication in response thereto. Defect analyzer 52 outputs indications of defects 61, such as relating to defects in the presence, location or formation of features, whether as a result of faulty manufacture or faulty design. At least some indications of defects may be included in a defect report 62.

Reference image 60 is provided by a reference image generator 64, which derives reference image 60, e.g., from a CAM data base or from the inspection image of an electrical circuit that is known to be not defective.

In an embodiment of system 10, a post processor 66 is provided. Post processor 66 is an optional feature of the invention, and is not required in all embodiments. In an embodiment of the invention, post processor 66 is provided as a software image analyzer running on general purpose hardware. Alternatively, it may run on suitable dedicated hardware. Post processor 66 receives, as inputs, topology representation 44, and one or more indications of defects 61 from analyzer 52, and an indication of regions of interest 70 which require height inspection. Regions of interest 70 may be indicated off line prior to inspection and may be provided, e.g., by reference generator 64. Optionally, indications of defects 61 are also supplied to reference generator 64, and regions of interest 70 then may include regions of interest that are indicated off line and some regions of interest surrounding indications of defects 61. The functionality of indicating regions of interest may be provided by the same unit that supplies reference image 60, as shown, or by a separate unit.

Although indications of defects are shown in FIGS. 1 and 2 as being provided to post processor 66 by analyzer 52 based on analysis of height data, it is appreciated that indications of defects received from any other suitable processor, for example a processor analyzing fluorescent emission or reflectance, may be employed.

Regions of interest 70 that are indicated off line may be parts of electrical circuit 18 for which the inspection of a height (or depth) dimension has particular relevance. Such regions include, for example, vias 34 or blind vias (not shown) in which the inspection of height can be helpful to determine whether a via has been drilled to the proper depth and whether any debris remains therein; or some conductors 30 such as relatively long and thin conductors in which changes in height are likely to affect impedance, or otherwise adversely affect function of the electrical circuit; or solder paste deposits on a PCB prior to adhering an integrated circuit or ball grid array substrate, e.g. using SMT type mounting techniques, to ensure the proper volume of solder paste.

It is appreciated that height inspection typically requires greater resources and inspection flexibility compared to binary inspection processes. As such, height inspection typically is more suited to be performed in an off-line or semi-off line inspection process in a manner that is limited to selected portions of an image requiring further inspection and analysis, and not on the entire surface. Accordingly, in some exemplary embodiments of the invention height inspection is performed on the entire surface, while in other exemplary embodiments of the invention height inspection is performed only on selected portions of the surface.

Regions requiring height inspection thus may be indicated, e.g., in a host application by specifying a window of interest around each region that requires height inspection. It is appreciated that, for regions requiring special attention for height inspection, inputs from topology representation 44 obtained during an initial inspection mode may be employed; alternatively, additional images such of regions requiring special attention for height inspection may be obtained, e.g., at an increased resolution, co-temporally with a main inspection or in addition thereto.

Post processor 66 may be operative to inspect topology representation 44 (or additionally obtained topology images of regions of interest (not shown)), with localized inspection algorithms which analyze the height at selected locations. The locations inspected by post processor 66 may be those locations indicated by defect analyzer 52 as having possible defects which require height inspection, e.g., fine shorts 68 between adjacent conductors, or locations of interest 70 that are chosen off tine. Thus, in accordance with some embodiments of the invention, a real defect is reported wherever a defect is indicated by analysis of both a reduced representation 50, e.g. relating to defects in the planar geometry of an article being inspected, and a topology representation 44 thereof. Thus, a real defect exhibits both a planar difference when compared to a reference, as well as height difference. Alternatively, defects are reported wherever a planar defect or a height defect is encountered. Other logic may also be employed. Thus for example, a defect may be reported wherever a planar defect is found, provided that the defect is confirmed by height inspection, or wherever a height defect is found in region of interest that is defined offline. A system for analysis of multiple attributes of an image to determine defects therein is described in U.S. patent application Ser. No. 10/032,098 entitled, "Electrical Circuit Conductor Inspection", which is being filed concurrently herewith, the disclosure of which is incorporated by reference, in its entirety, for its useful background information on such a system for analyzing multiple attributes.

It is also appreciated that the above referenced invention is suitable for use in an electrical circuit manufacturing facility. In an electrical circuit manufacturing process, a portion of an electrical circuit is deposited on a substrate, and the systems and methods described hereinabove are employed to inspect the electrical circuit for defects. Any substrates that are found to include defective portions are either repaired or discarded, such that only those substrates which pass defect inspection using the above described systems and methodologies are used.

It is understood by those familiar with this field that the present invention is not limited by what has been particularly shown and described hereinabove. Many and various modifications are possible without departing from the scope and spirit of the invention, and will readily occur to those familiar with this field. As one exemplary modification among many possible, various types of height sensor assemblies may be used, such as a conoscopic holographic probe (commercially available under the name CONOPROBE from OPTIMET Optical Metrology Ltd of Jerusalem, Israel), a scanning height profiler described in copending U.S. patent application No. 60/307,606, or stereoscopic imaging systems available from Envision Advanced Medical Systems Ltd. of Petah Tikva, Israel.

Therefore, the scope of the present invention includes both combinations and subcombinations of the features described hereinabove as well as modifications and variations thereof which would occur to a person of skill in the art upon reading the foregoing description and which are not in the prior art. The scope of the invention should thus be understood to be described not by the specific examples presented above, but by the claims presented below.

What is claimed is:

1. An automated optical inspection system for inspecting electrical circuits comprising:

a sensor arranged with respect to a surface of an electrical circuit being inspected, said sensor sensing a height dimension associated with a plurality of elemental regions on said surface;

a processor in communication with said sensor, operative to receive height data for said plurality of elemental regions and to produce a planar representation of said surface based on said height data;

an analyzer in communication with said processor, operative to receive and analyze said planar representation, and to determine therefrom defects in said electrical circuit; and wherein said planar representation is a multi-population representation of at least some parts of said electrical circuit indicating the locations of at least some parts which extend above said surface and indicating the locations of at least some parts which extend below said surface.

2. An automated optical inspection system for inspecting electrical circuits for defects according to claim 1, wherein the height data for said plurality of elemental regions forms a topology representation of said surface.

3. An automated optical inspection system for inspecting electrical circuits for defects according to claim 1, wherein said reduced representation does not indicate a height dimension.

4. An automated optical inspection system for inspecting electrical circuits for defects according to claim 1, wherein said at least some parts comprise one or more of conductors, opens, and shorts.

5. An automated optical inspection system for inspecting electrical circuits for defects according to claim 1, wherein said at least some parts comprise vias.

6. An automated optical inspection system for inspecting electrical circuits for defects according to claim 1, wherein said planar representation is a binary representation of at least some parts of said electrical circuit.

7. An automated optical inspection system for inspecting electrical circuits for defects according to claim 1, wherein said reduced planar representation indicates the shapes of said at least some parts of said electrical circuit which extend above or below said surface.

8. An automated optical inspection system for inspecting electrical circuits for defects according to claim 1, wherein said multi-population representation does not indicate a height dimension other than whether said element extends above or below said surface.

9. An automated optical inspection system for inspecting electrical circuits for defects according to claim 1, wherein said parts that extend above said surface are at least one of conductors and integrated circuits, and said parts that extend below said surface are vias.

10. An automated optical inspection system for inspecting electrical circuits for defects according to claim 1, wherein said sensor comprises a non-contact probe.

11. An automated optical inspection system for inspecting electrical circuits for defects according to claim 1 wherein said sensor comprises a range profiling camera.

12. An automated optical inspection system for inspecting electrical circuits for defects, comprising:

a sensor arranged with respect to a surface of an electrical circuit being inspected, said sensor sensing a height dimension associated with a plurality of elemental regions on said surface;

a processor in communication with said sensor, operative to receive height data for said plurality of elemental regions and to produce a planar representation of said surface based on said height data;

an analyzer in communication with said processor, operative to receive and analyze said planar representation, and to determine therefrom possible defects in said electrical circuit; and a post processor, in communication with said sensor and with said analyzer, said post processor being operative to receive said height data and an indication of the locations of at least some defects in said electrical circuit, and to process said height data at said locations to make an actual defect determination.

13. An automated optical inspection system for inspecting electrical circuits for defects, comprising:

a sensor arranged with respect to a surface of an electrical circuit being inspected, said sensor sensing a height dimension associated with a plurality of elemental regions on said surface;

a processor in communication with said sensor, operative to receive height data for said plurality of elemental regions and to produce a planar representation of said surface based on said height data;

an analyzer in communication with said processor, operative to receive and analyze said planar representation, and to determine therefrom defects in said electrical circuit; and a post processor, in communication with said sensor, operative to receive indications of locations of interest requiring analysis of said height data, and operative to process said height data at said locations of interest to determine the presence of defects.

14. An automated optical inspection system for inspecting electrical circuits for defects, comprising:

a sensor arranged with respect to a surface of an electrical circuit being inspected, said sensor sensing a height attribute associated with ones of a plurality of elemental regions on said surface;

a first processor receiving and processing a first inspection input comprising a sensed attribute for said ones of said plurality of elemental regions to provide an indication of a possible defect in said electrical circuit; and a second processor receiving and processing a second inspection input comprising said height attribute associated with selected ones of said plurality of elemental areas located in a region surrounding said indication of possible defect to provide an indication of an actual defect in said electrical circuit.

15. An automated optical inspection system according to claim 14 wherein said first inspection input comprises said sensed height attribute.

16. An automated optical inspection system according to claim 14 and wherein said first inspection input is supplied by said sensor sensing said height attribute.

17. An automated optical inspection system according to claim 14 and further comprising inspection apparatus having a second sensor in addition to said sensor sensing said height attribute.

18. An automated optical inspection system according to claim 14 and further comprising inspection apparatus providing said first inspection input, said first inspection input corresponding to an optically sensible attribute other than height.

19. An automated optical inspection system according to claim 18 and wherein said first inspection input comprises at least one of an optically sensible attribute selected from the group consisting of: a fluorescence emission and a reflectance.

20. An automated optical inspection system according to claim 18 and wherein said first inspection input corresponds to an image of an electrical circuit to be inspected, and said height attribute is acquired only for portions of the electrical circuit indicated as requiring further inspection.

21. An automated optical inspection system according to claim 18 and wherein said first inspection input corresponds to an image of an electrical circuit to be inspected, and said height attribute is acquired at least for portions of an electrical circuit indicated as requiring further inspection.

22. An automated optical inspection system according to claim 14 and wherein said sensor is operative to sense said height attribute in an off-line or semi-offline inspection process in response to said first processor processing said first inspection input.

23. A method of optical inspection for inspecting electrical circuits for defects, comprising:

sensing a height attribute associated with ones of a plurality of elemental regions on a surface of an electrical circuit;

receiving and processing a first inspection input comprising a sensed attribute for said ones of said plurality of elemental regions;

indicating a possible defect in said electrical circuit in response to said processing said first inspection input;

receiving and processing a second inspection input comprising said height attribute associated with selected ones of said plurality of elemental areas located in a region surrounding said indication of possible defect; and indicating an actual defect in said electrical circuit in response to said processing said second inspection input.

24. A method of optical inspection according to claim 23 and wherein said receiving and processing a first inspection input comprises receiving and processing a sensed height attribute.

25. A method of optical inspection according to claim 23 and wherein said receiving and processing a first inspection input comprises receiving and processing a first inspection input corresponding to an optically sensible attribute other than height.

26. A method of optical inspection according to claim 25 and wherein said receiving and processing a first inspection input other than height comprises receiving and processing an optically sensible attribute selected from the group consisting of: a fluorescence emission and a reflectance.

27. A method of optical inspection according to claim 23 and wherein said receiving and processing a first inspection input comprises receiving and processing an optical image of an electrical circuit to be inspected, and wherein said receiving and processing a second inspection input comprising a height attribute is performed only for portions of the electrical circuit indicated as requiring further inspection.

28. A method of optical inspection according to claim 23 and wherein said receiving and processing a first inspection input comprises receiving and processing an optical image of an electrical circuit to be inspected, and wherein said receiving and processing a second inspection input comprising a height attribute is performed at least for portions of the electrical circuit indicated as requiring further inspection.

29. A method of optical inspection according to claim 28 and wherein said receiving and processing a second inspection input comprising a height attribute is performed substantially for an entire electrical circuit.

30. A method of optical inspection according to claim 23 and wherein said receiving and processing a second input comprising said height attribute is performed in an off-line or semi-offline inspection process in response to said first processor receiving and processing said first inspection input.

31. A method for manufacturing electrical circuits, comprising:
  forming an part of electrical circuit on an electrical circuit substrate;
  optically inspecting said electrical circuit substrate, said optically inspecting comprising:
    sensing a height attribute associated with ones of a plurality of elemental regions on a surface of an electrical circuit;
    receiving and processing a first inspection input comprising a sensed attribute for said ones of said plurality of elemental regions;
    indicating a possible defect in said electrical circuit in response to said processing said first inspection input;
    receiving and processing a second inspection input comprising said height attribute associated with selected ones of said plurality of elemental areas located in a region surrounding said indication of possible defect; and
    indicating an actual defect in said electrical circuit in response to said processing said second inspection input.

32. A method for manufacturing electrical circuits according to claim 31 and wherein said receiving and processing a first inspection input comprises receiving and processing a sensed height attribute.

33. A method for manufacturing electrical circuits according to claim 31 and wherein said receiving and processing a first inspection input comprises receiving and processing a first inspection input corresponding to an optically sensible attribute other than height.

34. A method for manufacturing electrical circuits according to claim 33 and wherein said receiving and processing a first inspection input other than height comprises receiving and processing an optically sensible attribute selected from the group consisting of: a fluorescence emission and a reflectance.

35. A method for manufacturing electrical circuits according to claim 31 and wherein said receiving and processing a first inspection input comprises receiving and processing an optical image of an electrical circuit to be inspected, and wherein said receiving and processing a second inspection input comprising a height attribute is performed only for portions of the electrical circuit indicated as requiring further inspection.

36. A method for manufacturing electrical circuits according to claim 31 and wherein said receiving and processing a first inspection input comprises receiving and processing an optical image of an electrical circuit to be inspected, and wherein said receiving and processing a second inspection input comprising a height attribute is performed at least for portions of the electrical circuit indicated as requiring further inspection.

37. A method of optical inspection according to claim 36 and wherein said receiving and processing a second inspection input comprising a height attribute is performed substantially for an entire electrical circuit.

38. A method for manufacturing electrical circuits according to claim 31 and wherein said receiving and processing a second input comprising said height attribute is performed in an off-line or semi-offline inspection process in response to said first processor receiving and processing said first inspection input.

* * * * *